(12) United States Patent
Slatkin et al.

(10) Patent No.: US 9,233,260 B2
(45) Date of Patent: Jan. 12, 2016

(54) MAGNETIC CONFINEMENT FOR MICROBEAM RADIATION DAMAGE AREA

(71) Applicant: MICROBEAM THERAPY, LLC, Redwood City, CA (US)

(72) Inventors: Daniel N. Slatkin, Essex, CT (US); Fred Harden Geisler, Chicago, IL (US)

(73) Assignee: MICROBEAM THERAPY, LLC., Redwood City, CA (US)

( * ) Notice: Subject to any disclaimer, the term of this patent is extended or adjusted under 35 U.S.C. 154(b) by 414 days.

(21) Appl. No.: 13/853,448

(22) Filed: Mar. 29, 2013

(65) Prior Publication Data

US 2014/0294154 A1 Oct. 2, 2014

(51) Int. Cl.
*A61N 5/10* (2006.01)

(52) U.S. Cl.
CPC ....... *A61N 5/1042* (2013.01); *A61N 2005/1095* (2013.01)

(58) Field of Classification Search
CPC .................. A61N 2005/1091; A61N 5/1084; A61N 5/1042; A61N 5/1064; A61N 2005/1095; A61N 5/1049; A61N 2005/1076; A61N 2005/1097; A61N 2005/1098; A61N 5/1068; A61N 5/1078; A61N 1/36021; A61N 2005/1061; A61N 2005/1087; A61N 2/002; A61N 5/10; A61N 5/1031; A61N 5/1043; A61N 5/1044; A61N 5/1045; A61N 5/1048; A61N 5/1081; A61N 2005/1074; A61N 5/1065; A61N 5/1079; A61N 5/1069; A61N 5/1077; G21K 1/10
USPC ................................ 378/62, 65, 92, 137, 138
See application file for complete search history.

(56) References Cited

U.S. PATENT DOCUMENTS

| 4,755,685 | A | 7/1988 | Kawanami |
| 5,339,347 | A | 8/1994 | Slatkin |
| 5,771,270 | A | 6/1998 | Archer |
| 7,283,610 | B2 * | 10/2007 | Low ..................... A61N 5/1084 378/197 |
| 8,915,833 | B1 * | 12/2014 | Sahadevan ........... A61N 5/1027 600/1 |
| 2006/0176997 | A1 | 8/2006 | Dilmanian |
| 2010/0329413 | A1 | 12/2010 | Zhou |

OTHER PUBLICATIONS

Notification of Transmittal of the International Search Report and the Written Opinion of the International Searching Authority, or the Declaration.
Ahunbay et al, "Direct Aperture Optimization-Based Intensity-Modulated Radiotherapy for Whole Breast Irradiation", Int. J. Radiation Oncology Biol. Phys., vol. 67, No. 4, 2007, pp. 1248-1258.
Slatkin et al, "Prospects for Microbeam Radiation Therapy of Brain Tumours in Children", Medical Department Brookhaven National Laboratory, 2008, p. 163.

(Continued)

*Primary Examiner* — Irakli Kiknadze
(74) *Attorney, Agent, or Firm* — Kramer Amado P.C.

(57) ABSTRACT

Various embodiments relate to a method of performing microbeam radiation therapy on a subject, including: producing a high-energy radiation beam in a first direction; producing planar microbeams using the high-energy radiation beam in the first direction, wherein the microbeams have a width, wherein the planar microbeams produce scattered electrons; and applying a magnetic field in a direction lying in a plane substantially parallel to the planar microbeams, wherein the strength of the magnetic field corresponds to the width of the microbeam.

20 Claims, 2 Drawing Sheets

(56) References Cited

OTHER PUBLICATIONS

W.P.M. Mayles, "Survey of the Availability and Use of Advanced Radiotherapy Technology in the UK", Clinical Oncology 22 (2010) pp. 636-642.
Beilajew, "The Effect of Strong Longitudinal Magnetic Fields on Dose Deposition from Electron and Photon Beams", Med. Phys. 20 (4), Jul./Aug. 1993, pp. 1171-1179.
Keall et al, "Electromagnetic-Guided Dynamic Multileaf Collimator Tracking Enables Motion Management for Intensity-Modulated ARC Therapy", Int. J. Radiation Oncology Biol. Phys., vol. 79, No. 1, 2011, pp. 312-320.
E. Brauer-Krisch et al, "Characterization of a Tungsten/Gas Multislit Collimator for Microbeam Radiation Therapy at the Europeam Synchrotron Radiation Facility", Review of Scientific Instruments 76, 2005, 7 pages.
E. Brauer-Krisch et al, "Effects of Pulsed, Spatially Fractionated, Microscopic Synchrotron X-Ray Beams on Normal and Tumoral Brain Tissue", Mutation Research 704/Reviews in Mutation Research, (2010), pp. 160-166.
E. Brauer-Krisch, "New Technology Enables High Precision Multislit Collimators for Microbeam Radiation Therapy", Review of Scientific Instruments 80, (2009), 6 pages.
Jian-Rong Dai et al, "Intensity-Modulation Radiotherapy Using Independent Collimators: An Algorithm Study", Med. Phys. 26 (12), 1999, pp. 2562-2570.
Hargrave et al, "Diffuse Brainstem Glioma in Children: Critical Review of Clinical Trials", http://oncology.thelancet.com, vol. 7, 2006, pp. 241-248.
Kalef-Ezra, "Health Physics Aspects in Treatment Rooms After 18-MV X-Ray Irradiations", Radiation Protection Dosimetry (2011), vol. 147, No. 1-2, pp. 1-6.
J.A. Laissue et al, "Prospects for Microbeam Radiation Therapy of Brain Tumours in Children to Reduce Neurological Sequelae", Developmental Medicine & Child Neurology, 2007, 49: 577-581.
Laissue et al, "The Weanling Piglet Cerebellum: A Surrogate for Tolerance to MRT (Microbeam Radiation Therapy) in Pediatric Neuro-Oncology", Proceedings of SPIE, vol. 4508 (2001), pp. 65-73.
Fan et al, "Intensity Modulation Under Geometrical Uncertainty: A Deconvolution Approach to Robust Fluence", Physics in Medicine and Biology 55 (2010), pp. 4029-4045.
Bert et al, "Motion in Radiotherapy: Particle Therapy", Physics in Medicine and Biology 56 (2011), pp. R113-R144.
Serduc et al, High-Precision Radiosurgical Dose Delivery by Interlaced Microbeam Arrays of High-Flux Low-Energy Synchrotron X-Rays, Synchrotron X-Ray Radiosurgery, vol. 5, issue 2, 2010, pp. 1-12.
Slatkin, "Uniaxial and Biaxial Irradiation Protocols for Microbearn Radiation Therapy", Institute of Physics Publishing, Phys. Med. Biol. 49 (2004), pp. N203-N204.
Slatkin, "Tetrahedral Irradiation Protocol for Microbeam Radiation Therapy", Institute of Physics Publishing, Phys. Med. Biol. 51 (2006), pp. N295-N297.
Cai et al, "Targeted Cancer Therapy with Tumor Necrosis Factor-Alpha", Biochemistry Insights, 2008, pp. 5-21.
Gonsalves et al, "Tunable Laser Plasma Accelerator Based on Longitudinal Density Tailoring", Nature Physics, 2011, pp. 1-5.
Esteban et al. "Reducing the Number of Segments in Unidirectional Segmentations of Fluence Matrices for Multileaf Collimators in IMRT", M.Sc. Biomedical Engineering, 2010, pp. i-xii and 1-30.
DN Slatkin, "Prospects for Microbeam Radiation Therapy of Brain Tumours in Children", Medical Department, Brookhaven National Laboratory, p. 163.
International Search Report in corresponding PCT Application No. PCT/US2013/025267, issued on Apr. 3, 2013.

\* cited by examiner

MAGNETIC CONFINEMENT FOR MICROBEAM RADIATION DAMAGE AREA

TECHNICAL FIELD

Various exemplary embodiments disclosed herein relate generally to magnetic confinement for microbeam radiation damage area. Such application is especially useful in treating various cancers and other tumors and by concentration of the radiation to the selected area to be irradiated, and thus, reducing the radiation to areas not desired to be radiated.

BACKGROUND

Cancer continues to be one of the foremost health problems. Conventional treatments such as surgery and chemotherapy have been extremely successful in certain cases; in other instances, much less so. Radiation therapy has also exhibited favorable results in many cases, while failing to be completely satisfactory and effective in all instances. An alternative form of radiation therapy, known as microbeam radiation therapy (MBRS) or microbeam radiosurgery (MBRS) may be used to treat certain tumors for which the conventional methods have been ineffective.

MBRS differs from conventional radiation therapy by employing multiple parallel fan beams of radiation with a narrow dimension or thickness that may be on the order of 10 micrometers to 200 micrometers. The thickness of the microbeams is dependent upon the capacity of tissue surrounding a beam path to support the recovery of the tissue injured by the beam. It has been found that certain types of cells, notably endothelial cells lining blood vessels, but also oligodendroglial and other supporting cells, have the capacity to migrate over microscopic distances, infiltrating tissue damaged by radiation and reducing tissue necrosis in the beam path. In MBRS, sufficient unirradiated or minimally irradiated microscopic zones remain in the normal tissue, through which the microbeams pass, to allow efficient repair of irradiation-damaged tissue. As a result, MBRS is fundamentally different from other forms of radiation therapy.

In conventional forms of radiation therapy, including the radiosurgical techniques employing multiple convergent beams of gamma radiation, each beam is at least five hundred micrometers wide, so that the biological advantage of rapid repair by migrating or proliferating endothelial cells is minimal or nonexistent. Observations of the regeneration of blood vessels following MBRS indicate that endothelial cells cannot efficiently regenerate damaged blood vessels over distances on the order of more than 100 micrometers ($\mu$m). Thus, in view of this knowledge concerning radiation pathology of normal blood vessels, the skilled artisan may select a microbeam thickness as small as 20 $\mu$m but not more than 100 $\mu$m. Further, the microbeams may include substantially parallel, non-overlapping, planar beams with center-to-center spacing of from about 50 $\mu$m to about 500 $\mu$m. Also, the beam energies may range from about 30 to several hundred keV. These microbeams result in a dosage profile with peaks and valleys. The radiation dosage in the peaks is large enough to kill the targeted tumor, but also kills healthy cells in the peak dosage areas. The region between the peaks is called the valley region. The minimum radiation dosage in the valleys (i.e., the "nadir" valley dosage) is small enough to prevent clonogenically lethal damage to all potentially reparative cells in the valley dosage areas.

A division of a radiation beam into microbeams and the use of a patient exposure plan that provides non-overlapping beams in the tissue surrounding the target tumor allows the non-target tissue to recover from the radiation injury by migration of regenerating endothelial and other reparative cells of the small blood vessels to the areas in which the endothelial cells have been injured beyond recovery. Therefore, the probability of radiation-induced coagulative necrosis in normal, non-targeted tissue is lowered, which may improve the effectiveness of clinical radiation therapy for deep-seated and/or superficially situated tumors.

Various studies have shown the microbeam tissue-sparing effect for X-ray microbeams. Although other methods and processes are known for radiation therapy, none provides a method for performing radiation therapy while avoiding significant radiation-induced damage to tissues proximal to, distal to, and interspersed with the targeted lesion.

Present radiation therapies often take many days and weeks of treatment to provide enough radiation to a target tumor. On the other hand, MBRS can provide an effectual treatment in a single visit. Very high-energy radiation may be used with MBRS that results in the destruction of tumor tissue while allowing for the regeneration of healthy tissue affected by the microbeams.

Further, MBRS provides a method for treating cancerous tumors by using extremely narrow, quasi-parallel X-ray microbeams increasing the precision and accuracy of radiation therapy. MBRS also provides a method of using extremely small microbeams of radiation to unexpectedly produce effective radiation therapy while avoiding significant radiation-induced damage to non-targeted tissues.

A major benefit of MBRS is that the microbeams are so narrow that the vasculature of the tissue and other components of the tissue through which the microbeams pass can repair themselves by the infiltration of endothelial cells and other cells from surrounding unirradiated tissue. Present knowledge indicates that such infiltration can take place only over distances on the order of less than 500 $\mu$m and depends on the specific tissue being irradiated. The dimensions of the microbeams and the configuration of the microbeam array are therefore determinable with reference to the susceptibility to irradiation of the target tissue and the surrounding tissue to irradiation and the capacities of the various involved tissues to regenerate.

In MBRS it is possible to define an extraordinarily narrow penumbra (edge between the peak and valley regions) between the area radiated and the adjacent very low radiation area. Once the microbeams enter tissue they may be scattered and/or absorbed. The photoelectric effect and Compton scattering dominate the two interactions of the initial microbeam with the tissue. Both of these effects are photon-energy-dependent and the scattering angle distribution is well characterized in the physics literature. In both of these interactions electrons are emitted and may potentially go in any direction and may travel distances comparable to the width of the area irradiated by the microbeam. Some of these electrons will stay within the boundaries of the width of the irradiated area, which corresponds to a desired treatment area, while others will exit this area, and hence potentially damage untreated tissue. The electrons that exit the exact area of the initial microbeam treatment area and deposit their energy effectively act to blur the sharp line between the intensely irradiated area (peak) and the area of minimal radiation (valley). Widening of the penumbra (blurring at the edge between the peak and valley regions) is detrimental to the desired dose delivery and can: harm the adjacent healthy tissues; limit useful microbeam treatment depth; limit depths of tumors below the skin; limit the types of tumor/lesions/conditions treated; and limit the usefulness of MBRS in general.

Confining the radiation dose and/or damage geometry of the scattered electrons to the intended Microbeam treatment area (peaks) and out of the spared regions (valley) between the Microbeam peaks would enhance the efficacy of the radiation therapy. In some cases the spread of the radiation dose and/or damage region outside of the intended peak area would limit or prevent the usefulness of Microbeam treatment because of the detrimental effect of the radiation dose and/or damage in the unplanned valley regions.

U.S. Pat. No. 5,339,247 to Slatkin et al. titled Method for Microbeam Radiation Therapy provides additional background related to MBRS, and is hereby incorporated by reference for all purposes as if fully set forth herein.

SUMMARY

Accordingly, there is a need for improved radiation therapies that can quickly yet safely treat patients. Further there is a need to confine radiation doses in desired peak dosage areas will minimizing radiation doses in desired valley dosage areas.

A brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in the later sections.

Various embodiments may also relate to a method of performing microbeam radiation therapy on a subject, including: producing a high-energy radiation beam in a first direction; producing planar microbeams using the high-energy radiation beam in the first direction, wherein the microbeams have a width, wherein the planar microbeams produce scattered electrons; and applying a magnetic field in a direction lying in a plane substantially parallel to the planar microbeams, wherein the preferred minimum strength of the magnetic field is determined mainly by the separation between the microbeam, i.e., by the widths of the dose valleys. Thus the magnetic field will minimize the blurring (penumbra) of peak regions into the valley regions.

Further embodiments may also relate to a microbeam radiation therapy system, including: a high-energy radiation beam; a collimator with slits, wherein the collimator only passes the high-energy radiation beam through the slits; a beam filtering and limiting system; and a magnet producing a magnetic field in a direction substantially parallel to the slits of the collimator, wherein the magnetic field intersects the high-energy radiation beam that passes through the slits.

BRIEF DESCRIPTION OF THE DRAWINGS

In order to better understand various exemplary embodiments, reference is made to the accompanying drawings wherein.

DETAILED DESCRIPTION

Figure 1:
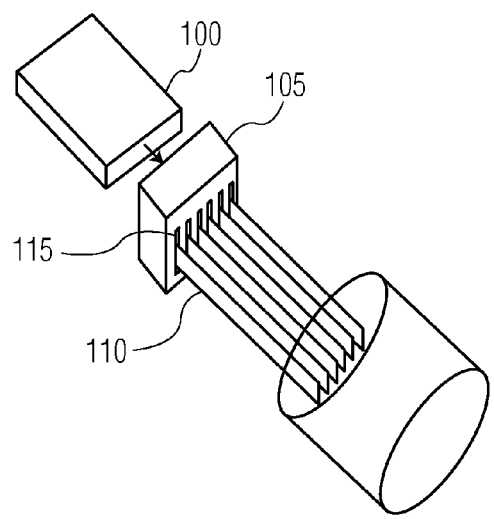
FIG. 1 illustrates a method for producing microbeams using a collimator.

Referring now to the drawings, in which like numerals refer to like components or steps, there are disclosed broad aspects of various exemplary embodiments.

FIG. 1 illustrates a method for producing microbeams using a collimator. The collimator 105 may include a plurality of parallel slits 115 in a vertical direction. A high-energy radiation fan beam 100 that may be narrow in the vertical direction and wide in the horizontal direction may pass through the collimator 105. Because the collimator 105 is made of a high-Z material, it blocks portions of the incident x-ray radiation of the high-energy radiation fan beam 100. The portion of the high-energy radiation fan beam 100 that passes through the slits 115 of the collimator 105 forms the microbeams 110. The microbeams 110 may be used to treat a subject. Depending upon the vertical height of the fan beam 100 relative to the size of the treatment area, the subject may have to be moved relative to the microbeams 110 in order to irradiate the whole treatment area. Typically, it is not possible to move the high-energy radiation fan beam 100 because of the massive size of the facility necessary to produce the high-energy radiation fan beam 100.

MBRS may apply very high-energy radiation beams for a very short period of time and in some cases for a fraction of a second. One problem with MBRS may occur when scattered electrons are emitted in the treatment area due to the photoelectric and Compton effects, which scattered electrons my then enter the non-treatment area (valley regions). This may result in smearing of the peak and valley doses applied to the subject. Effective and safe MBRS relies upon valley dose areas in which the radiation dose is low enough to prevent any damage to the healthy cells.

The photoelectric effect causes electrons to be emitted from irradiated matter as a consequence of absorption of energy by the irradiated matter from electromagnetic radiation of very short wavelength and high frequency, such as, for example, incident ultraviolet or X-ray radiation. Compton scattering is an inelastic scattering of a photon by a free charged particle, usually an electron. Compton scattering results in a decrease in energy (increase in wavelength) of the photon (which may be an X-ray or gamma ray photon), called the Compton effect. Part of the energy of the photon is transferred to the scattering electron. Both these effects may produce scattered electrons that deposit their energy and, directly or indirectly, damage healthy tissues in the valley region.

Figure 3:
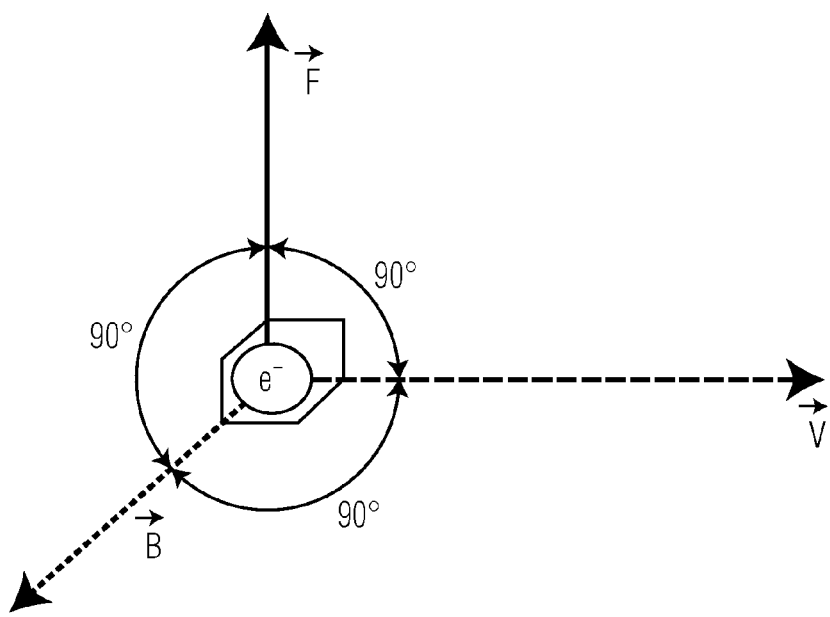
FIG. 3 the force applied to a moving electron by a magnetic field.

A magnetic field may be applied to substantially confine such scattered electrons to the treatment area and hence limit their contribution of radiation damage in the valley regions. Suppose that a charged particle like an electron is moving in a magnetic field and that the direction of the motion is at right angles to that field. The result is that the electron is acted upon by an electromagnetic force F which is perpendicular both to the direction of the field and to the direction of the velocity of the particle. FIG. 3 illustrates this scenario where an electron has a velocity along the x axis and a magnetic field with a direction along the z axis.

The magnitude of the force depends on the charge of the electron e, its velocity v, and the magnetic field B:

$$F = evB. \quad (1)$$

Figure 4:
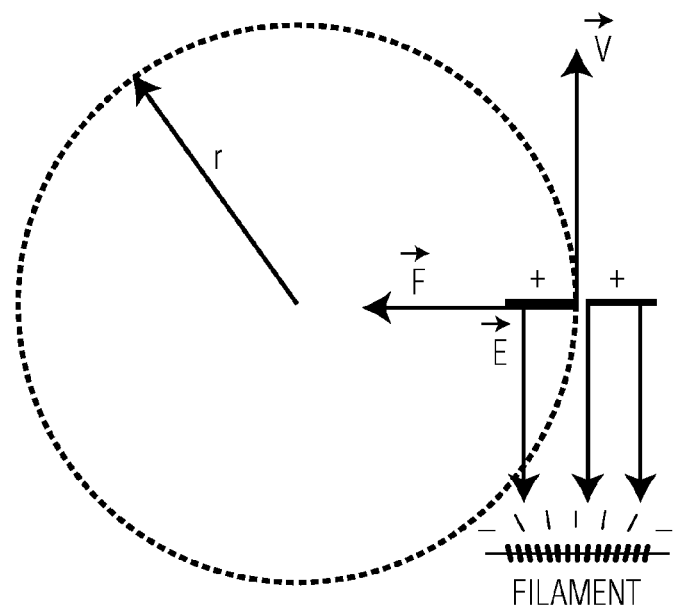
FIG. 4 illustrates the circular path of an electron in a uniform magnetic field.

Because the resulting force is perpendicular to the velocity, it causes the electron to move in a circular path of radius r which is illustrated in FIG. 4.

Hence F is a centripetal force:

$$F = \frac{mv^2}{r}. \quad (2)$$

Equating equations 1 and 2, we have $$F = evB = \frac{mv^2}{r}. \quad (3)$$
$$\Rightarrow eB = \frac{mv}{r}$$

This gives us the expression $$r = \frac{mv}{Be}. \quad (4)$$

Thus, for example, a 1 Tesla magnetic field would cause 10 Kev secondary electrons to spin in a circle with a radius of 337 µm. This magnetic field could be in any direction or axis and the resultant circular electron motion would spin around the axis of the magnetic field and contain any component of the electron movement perpendicular to the axis of the radiation. The component of the velocity parallel to the axis of the magnetic field would not be affected by the magnetic field. Therefore, placing an axis of a magnetic field parallel to the plane of the microbeams would allow movement of the electron within the treatment area of the peaks while decreasing electron movement outside the treatment area in the valley regions.

The strength of the magnetic field may be chosen to minimize the number of scattered electrons that may leave the treatment area. The resulting radius of motion of the scattered electrons may be selected to be less than a fraction of the peak with such as 0.01 to 0.2 (for example, 0.01, 0.05, 0.1, or 0.2) of the thickness of the microbeams. Even lower fractional values of the peak width values may be used if practicable. The level of containment of the secondary electrons depends on the strength of magnetic field and the energy/velocity of the scattered electrons. Further, the energy/velocity of the electrons depends upon the specific spectral characteristics of the radiated energy in the microbeams. Also, the specific composition of the treatment area (i.e., bone, muscle, fat, air, etc.) may affect the number of scattered electrons. All of these parameters may be taken into account to determine the magnitude of the magnetic field needed to provide the desired and practicable containment of the scattered electrons.

Prior to treatment of the subject, detailed three-dimensional measurements may be made of the treatment area as well as modeling with a physical and/or virtual phantom of the zone to be irradiated to determine the optimal treatment. Information from these measurements and phantom modeling may be further used to determine the level of containment of the scattered electrons.

Figure 2:
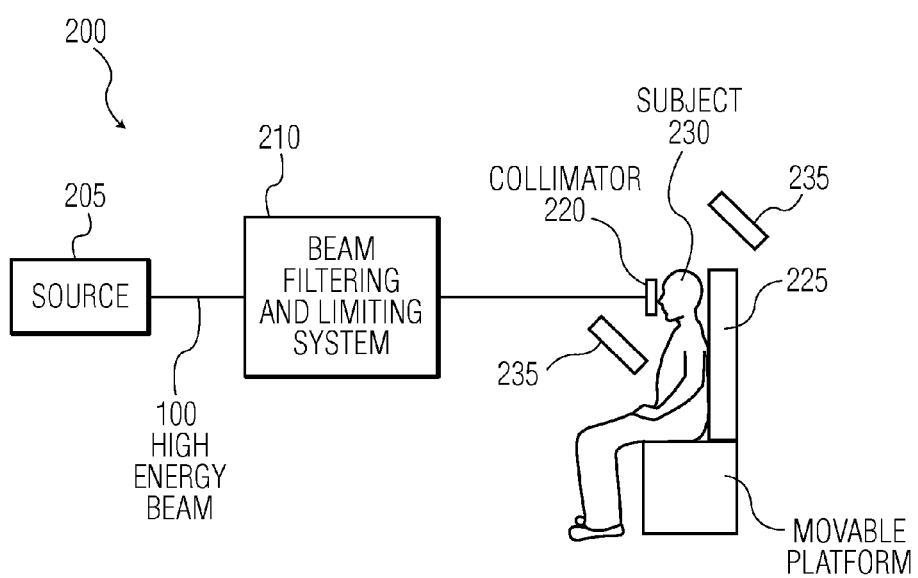
FIG. 2 illustrates an embodiment of a MBRS system.

FIG. 2 illustrates an embodiment of a MBRS system. The MBRS system 200 may include a source 205 that produces a high-energy fan beam 100, a beam filtering and limiting system 210, a collimator 220, a movable platform 225, and magnets 235. A subject 230 may be treated by the MBRS system 200.

The source 200 may produce high-energy electromagnetic radiation beam such as X-ray or gamma radiation beam. High-energy X-ray radiation may be especially beneficial. In any generated photon beam, the photons are produced having a characteristic spectrum of energies. The photon energy of the beams may range optimally from about 30 keV to about 300 keV.

A synchrotron may be used to generate an X-ray beam having practically no divergence and a high fluence rate. These synchrotron generated X-rays have the potential for projecting sharply defined beam edges deep in the body. This source may be useful for generating X-ray microbeams for radiobiology, radiotherapy, and radiosurgery. A high fluence rate is required to implement MBRS because exposure times must be short enough (e.g., less than about 1 second) to avoid the blurring of margins of the irradiated zones of tissue due to body or organ movements. In some cases a fraction of a second to prevent blurring of normal cardiac motion. Absorbed doses to non-targeted tissues (i.e., in tissues both proximal and distal to the isocentric target where the microbeams do not overlap) situated between microbeams may be kept below the threshold for radiation damage. These factors make it possible to effectively irradiate a target using a field of many well defined, closely spaced microbeams.

The radiation beam for producing the microbeam array may be obtained from industrial X-ray generators or from synchrotron beamlines at electron storage rings. The radiation beam may be obtained from a wiggler or undulator inserted in an electron storage ring. A conventional "planar" wiggler uses periodic transverse magnetic fields to produce a beam with a rectangular cross-section, typically having a horizontal to vertical beam opening angle ratio on the order of 50:1. In an alternative embodiment, the radiation beam is obtained from a "helical" wiggler, a configuration capable of producing a substantially less anisotropic beam. While a fan beam is discussed in the embodiment below, it is also possible to place the subject to be treated a large distance (i.e., >100 m) from the source 205, which may allow the X-ray beam from the source to expand enough in both the horizontal and vertical directions so that the beam covers the whole treatment area, and hence, it may not be necessary to move the subject relative to the high-energy beam. Further, such beam-spreading could be accomplished by two orthogonal wigglers that would spread the beam first in one direction and then in a second orthogonal direction. Such embodiments would not require movement of the subject, but the collimator may still be affixed to the subject as with the previously described embodiments. In another alternative embodiment, bending magnets may be used to spread the beam. For example, many synchrotrons may include a plurality of straight sections connected by bent sections where the beam is bent from straight section to the adjacent section. The beam may be recovered from the bent section of the synchrotron using a wiggler that would result in a spread beam. Alternatively, the bender connecting adjacent straight sections may itself be a wiggler, i.e., a "wiggler-bender," in which each successive centripital force on any particular circulating bunch of electrons is slightly more forceful than the preceding centrifugal force on the same bunch. This would not only result in a spread X-ray beam but would make appropriate medical use of space at the facility presently occupied by a simple bending magnet emitting X-rays of energy below those that might be useful for MBRS: the forceful "wiggles" in a wiggler-bender would assure a higher median energy of X-rays emitted tangentally therefrom than would be the case without "wiggles" in the bender.

The beam filtering and limiting system 210 filters and limits the high-energy beam 100 for treating the subject 230. As mentioned above the source may produce a high-energy beam with a range of energies. Often only a certain range of energies may be used to treat the subject. Accordingly, various filters made of various materials may be placed in the path of the high-energy beam to filter out the undesired energy bands in the high-energy beam. Further, spatial limiting may be used to limit the beam to the desired beam size and geometry. This may help to prevent unwanted and unsafe stray radiation from the source 200. Such spatial limiting may be accomplished, for example, with plates having slits. The plates may be of sufficient thickness and high-Z material to block portions of the high-energy beam from the source 200 and act to maintain the radiation in the peak region and out of the valley region. Further, examples of spatial limiting are described in U.S. patent application Ser. No. 13/853,331 entitled, "Low Dose-rate Radiation for Medical and Veterinary Therapies with Three Dimensionally Shaped Profiles," filed concurrently herewith and which is hereby incorporated by reference for all purposes as if fully set forth herein.

The high-energy fan beam 100 may irradiate the collimator 220. As described above with respect to the FIG. 1, the collimator 220 may include a plurality of slits. The slits split the high-energy fan beam 100 into a plurality of microbeams 110 (as shown in FIG. 1). The collimator 220 may be affixed securely to the subject. As a result, the micro beams formed by the collimator 220 are fixed relative to the subject, even if the subject moves. In other embodiments, the collimator 220 may affixed to other elements of the MBRS system 200, or even be affixed to its own movable or stationary platform.

The movable platform 225 may hold the subject in a fixed position and then move the subject relative to the high-energy fan beam 100. The movable platform 225 may be any known platform that secures the patient and then allows for very precise movement of the patient relative to the high-energy fan beam 100. In other embodiments, the subject may be placed on a stationary platform instead.

Magnets 235 may be positioned around the subjected 235 in order to produce a magnetic field in a plane parallel to the microbeams 110. The magnets 235 may be any type of magnet that may be capable of producing the needed magnetic field in the desired direction. For example, permanent magnets, electromagnets, super-conducting magnets, etc. may be used. The magnets may be positioned anywhere around the subject, but must be able to produce the needed magnetic field mainly in the non-targeted normal tissue order to contain the photoelectric effect and the Compton effect scattered electrons of the radiation in the peak regions, thereby optimizing the repair of normal tissues traversed by the peak-dose zones of the microbeam array. Although there might be a concomitant magnetic field imposed on the targeted zone, that part of the field would serve no useful purpose, indeed might promote the repair of the undesired targeted malignancy, were that possible: it has been shown, unexpectedly and favorably, that supporting cells in malignant tissues have little self-repair capacity after being lethally irradiated.

In one embodiment, the magnets 235 may be affixed to the collimator 220. In this embodiment the magnets may be aligned with the slits in the collimator 220 in order to contain the scattered electrons produced in the peak regions. Such an arrangement has the advantage that the magnetic field from the magnets 235 may be accurately aligned to the microbeams produced using the collimator 220.

In other embodiments, the magnets 235 may be separate from the collimator 220. In these embodiments, some sort of alignment apparatus and/or method may be used to align the magnetic field of the magnets. Such apparatus and/or methods my include mechanical systems, optical systems, magnetic field detectors, or other known alignment systems.

Because such high-energy radiation may be used in MBRS it is very important to precisely control the dose of radiation applied to the subject 230. Prior to treatment, a medical physicist may use sophisticated computer tools and modeling to determine the dosage parameters to use during the MBRS.

While the application of a single MBRS dose may be effective to effectively treat a subject, it may also be beneficial to provide multiple treatments from different directions. The treatment directions and doses would be selected to allow the multiple different sets of microbeams to intersect in the target area. These multiple doses of high-energy radiation to the treatment area may increase the effectiveness of the MBRS. Therefore, for each treatment direction, the magnets 235 may be repositioned to provide a magnetic field in a plane parallel to the microbeams to thus contain scattered electrons during treatment in each direction. In the area of intersection of with the microbeams, the tissue would be totally destroyed. However, this magnetic confinement would protect the valley regions in the non-irradiated regions.

While the high radiation beam 100 is described as being spread in the horizontal direction, it may be beneficial to spread the beam in the vertical direction or any other direction. Using other beam spreading directions may provide benefits in accurately delivering a dose. Also, if multiple MBRS treatments are used, then the ability to spread the high-energy beam 100 in various directions may be beneficial. For example, when producing high-energy X-rays using a synchrotron, a wiggler may be used to spread the beam in a desired direction. Such a wiggler may be mounted so that it can be rotated around an axis parallel to the high-energy beam. As a result the beam may be spread in any desired direction. The rotation of the wiggler may be precisely and accurately controlled to allow the beam to spread as needed to apply the desired radiation dose. Therefore, for each beam direction, the magnets 235 may be repositioned to provide a magnetic field in a plane parallel to the microbeams to thus contain scattered electrons during treatment in each direction.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

We claim:

1. A method of performing microbeam radiation therapy on a subject, comprising:
   producing a high-energy radiation beam in a first direction;
   producing planar microbeams using the high-energy radiation beam in the first direction, wherein the microbeams have a width, wherein the planar microbeams produce scattered electrons; and
   applying a magnetic field in a direction lying in a plane substantially parallel to the planar microbeams, wherein the strength of the magnetic field corresponds to the width of the microbeam,
   wherein the magnetic field is produced in non-targeted normal tissues of the subject.

2. The method of claim 1, wherein the magnetic field causes the scattered electrons in the magnetic field to move in a circular path with a radius in a plane substantially perpendicular to the direction of the applied magnetic field.

3. The method of claim 2, wherein radius is less than 0.2 of the width of the microbeams.

4. The method of claim 2, wherein radius is less than 0.1 of the width of the microbeams.

5. The method of claim 2, wherein radius is less than 0.05 of the width of the microbeams.

6. The method of claim 2, wherein radius is less than 0.01 of the width of the microbeams.

7. The method of claim 1, wherein the magnetic field is produced by a permanent magnet.

8. The method of claim 1, wherein the magnetic field is produced by an electromagnet.

9. The method of claim 8, wherein the magnetic field is produced by a super conducting magnet.

10. The method of claim 1, further comprising:
    producing a high-energy radiation beam in a second direction;
    producing second planar microbeams using the high-energy radiation beam in the second direction, wherein the microbeams have a second width, wherein the second planar microbeams produce scattered electrons; and
    applying a second magnetic field in a second direction lying in a plane substantially parallel to the second planar microbeams, wherein the strength of the magnetic field corresponds to the second width of the second microbeams.

11. A microbeam radiation therapy system, comprising:
a high-energy radiation beam;
a collimator with slits, wherein the collimator only passes the high-energy radiation beam through the slits;
a beam filtering and limiting system; and
a magnet producing a magnetic field in a direction substantially parallel to slits of the collimator, wherein the magnetic field intersects the high-energy radiation beam that passes through the slits, and wherein the magnetic field is produced in non-targeted normal tissues of a subject.

12. The system of claim 11, wherein the magnet produces a magnetic field that causes scattered electrons in the magnetic field to move in a circular path with a radius in a plane substantially perpendicular to the direction of the applied magnetic field.

13. The system of claim 12, wherein radius is less than 0.2 of the width of the microbeams.

14. The system of claim 12, wherein radius is less than 0.1 of the width of the microbeams.

15. The system of claim 12, wherein radius is less than 0.05 of the width of the microbeams.

16. The system of claim 12, wherein radius is less than 0.01 of the width of the microbeams.

17. The system of claim 11, wherein the magnet is a permanent magnet.

18. The system of claim 11, wherein the magnet is an electromagnet.

19. The system of claim 11, wherein the magnet is a super conducting magnet.

20. The system of claim 11, wherein the system is configured to provide radiation treatment in two different directions.

* * * * *